United States Patent
Rhim et al.

(10) Patent No.: US 7,591,845 B2
(45) Date of Patent: Sep. 22, 2009

(54) STENT FOR HIGH FREQUENCY THERMOTHERAPY

(75) Inventors: Hyun Chul Rhim, Seoul (KR); Kyong Min Shin, Seoul (KR)

(73) Assignee: Taewoong Medical Co., Ltd., Kyunggi-Do (KR)

( * ) Notice: Subject to any disclaimer, the term of this patent is extended or adjusted under 35 U.S.C. 154(b) by 37 days.

(21) Appl. No.: 10/546,227

(22) PCT Filed: Feb. 18, 2004

(86) PCT No.: PCT/KR2004/000329

§ 371 (c)(1),
(2), (4) Date: Oct. 17, 2005

(87) PCT Pub. No.: WO2004/073782

PCT Pub. Date: Sep. 2, 2004

(65) Prior Publication Data

US 2006/0161246 A1     Jul. 20, 2006

(30) Foreign Application Priority Data

Feb. 19, 2003   (KR)  ................. 20-2003-0004899 U
Feb. 3, 2004   (KR)  ..................... 10-2004-0006927

(51) Int. Cl.
*A61F 2/06* (2006.01)
(52) U.S. Cl. ..................................... 623/1.19; 623/1.44
(58) Field of Classification Search ............... 623/1.19, 623/1.18, 1.2, 1.27, 1.3, 1.31, 1.44, 1.32
See application file for complete search history.

(56) References Cited

U.S. PATENT DOCUMENTS

| 5,078,736 | A | | 1/1992 | Behl |
| 5,928,217 | A | * | 7/1999 | Mikus et al. ................. 604/530 |
| 6,156,061 | A | * | 12/2000 | Wallace et al. ............. 623/1.11 |
| 6,267,781 | B1 | | 7/2001 | Tu |
| 6,366,818 | B1 | | 4/2002 | Bolmsjo |
| 6,488,705 | B2 | * | 12/2002 | Schmitt et al. ............. 623/1.18 |
| 2001/0044647 | A1 | * | 11/2001 | Pinchuk et al. ............ 623/1.13 |

FOREIGN PATENT DOCUMENTS

KR     2002-80024     10/2002

\* cited by examiner

*Primary Examiner*—David Isabella
*Assistant Examiner*—Suba Ganesan
(74) *Attorney, Agent, or Firm*—Jordan and Hamburg LLP

(57) ABSTRACT

The object of this invention is to provide a stent for high frequency thermotherapy, which is fabricated by knitting first superlastic shape-memory alloy wires as a way to allow the first superelastic shape-memory alloy wires to cross each other at different positions to make a hollow cylindrical stent body having a net structure with a plurality of meshes. The stent body is covered with an insulating substance. A hollow cylindrical conductive body surrounds a waist part of the stent body while any one end or both ends of the conductive body is attached to the waist part of the stent body. At this time, the conductive body is fabricated by knitting second superelastic shape-memory alloy wires as a way to allow the second superelastic shape-memory alloy wires to cross each other at different positions.

4 Claims, 4 Drawing Sheets

STENT FOR HIGH FREQUENCY THERMOTHERAPY

TECHNICAL FIELD

The present invention relates, in general, to a stent for high frequency thermotherapy and, more particularly, to a stent for high frequency thermotherapy, which is made of a shape-memory alloy and used for insertion in a contracted target portion of an internal cavity with a lesion of a patient so as to expand the contracted target portion and to high-frequency heat the lesion in a tissue of the internal cavity to cauterize the lesion to necrotize the lesion, in addition to preventing the internal cavity from being re-contracted.

BACKGROUND ART

Generally, an internal cavity of a patient may be contracted or blocked due to diseases of the patient, leading to the functional deterioration and the functional disorder of the internal organs of the patient.

Moreover, the contraction or blockage of the internal cavity obstructs foods and biles, or blood from smoothly flowing in the stomach, the gullet, and the liver, or blood vessels of the patient, and may develop a complication.

In such a case, a contracted or blocked target portion of the internal cavity having a lesion must be expanded. At this time, for example, a stent may be effectively used to expand the target portion of the internal cavity with the lesion.

With reference to FIGS. 1 and 2, the conventional stent proposed by the inventor of this invention is fabricated by knitting superelastic shape-memory alloy wires 2 as a way to allow the superelastic shape-memory alloy wires 2 to cross each other at different positions to make a hollow cylindrical stent body 5 having a net structure with a plurality of diamond-shaped meshes 3. At this time, an insertion terminal and a discharge terminal, each having a plurality of curved portions positioned at regular intervals, are formed at both ends of the hollow cylindrical stent body 5. Additionally, the hollow cylindrical stent body 5 may be covered with clothes, vinyl-based materials, or artificial blood vessels.

When it is desired to insert the stent into the contracted portion of the internal cavity, the hollow cylindrical stent body 5 is primarily inserted into the contracted target portion of the internal cavity while being contracted in its diameter. Once the stent is inserted into the target portion of the internal cavity using an insertion tool, the stent elastically expands, due to superelasticity of the shape-memory alloy, to expand the contracted target portion of the internal cavity.

However, the conventional stent is used to only expand the contracted target portion of the internal cavity having the lesion, but not to heal the tissue with the lesion of the internal cavity.

Furthermore, the conventional stent covered with the clothes or the vinyl-based materials is problematic in that the stent may be movable within the slippery internal cavity due to smoothness of the clothes or the vinyl-based materials, and thus, the stent may be easily displaced from the target portion of the internal cavity.

DISCLOSURE OF THE INVENTION

Accordingly, the present invention has been made keeping in mind the above problems occurring in the prior art, and an object of the present invention is to provide an improved stent for high frequency thermotherapy, which is used for insertion in a contracted target portion of an internal cavity with a lesion of a patient in such a way that the stent is prevented from being undesirably displaced from the contracted target portion of the internal cavity so as to expand the contracted target portion. Furthermore, the stent high-frequency heats the lesion of the internal cavity to cauterize the lesion to necrotize the lesion, thereby preventing the internal cavity from being re-contracted.

Another object of the present invention is to provide a stent for high frequency thermotherapy, which obstructs a lesion of an internal cavity of a patient from radially protruding inward by use of an insulating substance constituting the stent to prevent the internal cavity from being contracted even though the necrotized lesion is regenerated.

Additional objects and/or advantages of the invention will be set forth in part in the description which follows and, in part, will be obvious from the description, or may be learned by practice of the invention.

The above and/or other objects are achieved by providing a stent for high frequency thermotherapy, which is fabricated by knitting first superelastic shape-memory alloy wires as a way to allow the first superelastic shape-memory alloy wires to cross each other at different positions to make a hollow cylindrical stent body having a net structure with a plurality of meshes. The stent has a double structure including the hollow cylindrical stent body covered with an insulating substance at inner and outer surfaces thereof, and a hollow cylindrical conductive body surrounding a waist part corresponding to a central part of the hollow cylindrical stent body while any one end or both ends of the hollow cylindrical conductive body is attached to the waist part of the hollow cylindrical stent body. At this time, the hollow cylindrical conductive body is fabricated by knitting second superelastic shape-memory alloy wires as a way to allow the second superelastic shape-memory alloy wires to cross each other at different positions.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
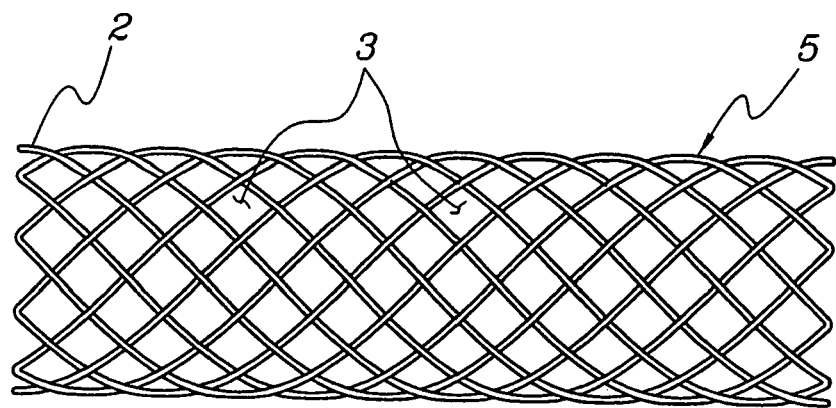
FIG. 1 is a front view of a conventional stent.
Figure 2:
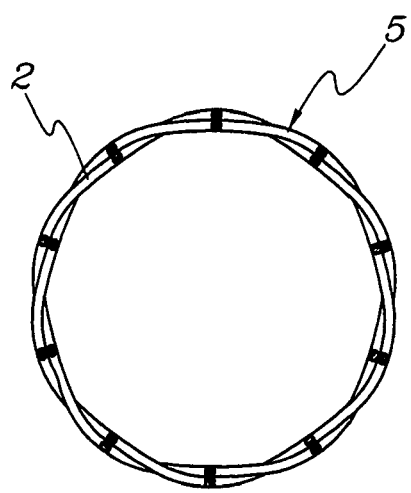
FIG. 2 is a side view of the stent of FIG. 1.

Reference should now be made to the drawings, in which the same reference numerals are used throughout the different drawings to designate the same or similar components.

Figure 3:
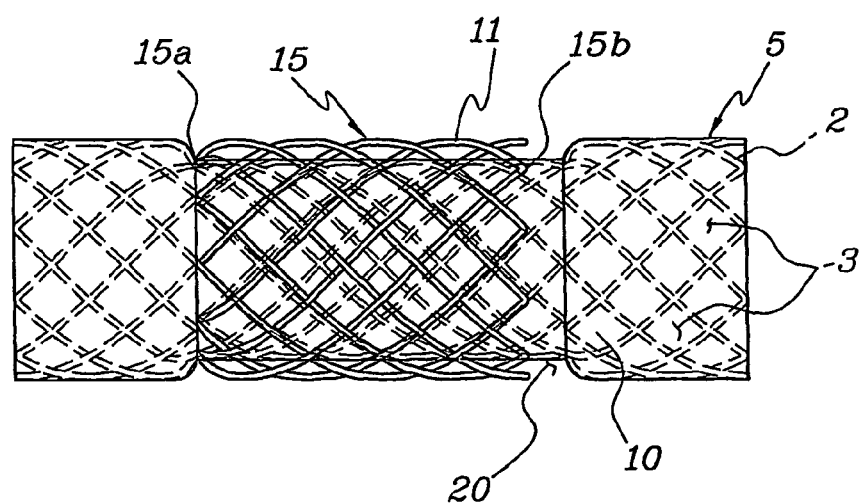
FIG. 3 is a front view of a stent according to the first embodiment of the present invention.
Figure 4:
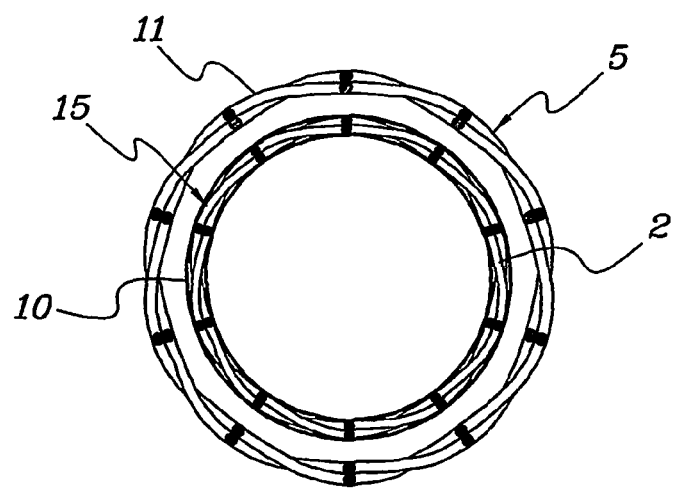
FIG. 4 is a side view of the stent of FIG. 3.

According to the first embodiment of the present invention, as shown in FIGS. 3 and 4, there is provided a stent for high frequency thermotherapy, which is fabricated by knitting first superelastic shape-memory alloy wires 2 as a way to allow the first superelastic shape-memory alloy wires 2 to cross each other at different positions to make a hollow cylindrical stent body 5 having a predetermined length and a net structure with a plurality of meshes 3. The stent includes an insulating substance 10 covered on inner and outer surfaces of the hollow cylindrical stent body 5. Furthermore, a hollow cylindrical conductive body 15 surrounds a waist part 20 corresponding to a central part of the hollow cylindrical stent body 5 while a first end 15a of the hollow cylindrical conductive body 15 is attached to the waist part 20 of the hollow cylindrical stent body 5 but a second end 15b of the hollow cylindrical conductive body 15 is not attached to the waist part 20. At this time, the hollow cylindrical conductive body 15 is fabricated by knitting second superelastic shape-memory alloy wires 11 as a way to allow the second superelastic shape-memory alloy wires 11 to cross each other at different positions.

In this respect, diameters of both ends of the hollow cylindrical stent body 5 are larger than a diameter of the central part, corresponding to the waist part 20, of the hollow cylindrical stent body 5, and the conductive body 15 surrounds the waist part 20 of the hollow cylindrical stent body 5 while the first end 15a of the conductive body 15 is attached to the waist part 20.

Needless to say, the waist part 20 is longer than the conductive body 15.

Additionally, a size of the hollow cylindrical stent body 5 depends on an inner diameter of an internal cavity of a patient, into which the stent body 5 is to be inserted, and a length of a lesion in a tissue of the internal cavity.

Further, the insulating substance 10 may be selected from any material including a polytetrafluoroethylene (PTFE) resin, a polyester(PE)-based resin, and a polyimide(PI)-based resin as long as the material has fire retardancy and elasticity so as to be freely changed against an external force in terms of a shape, and can prevent bacteria from penetrating therethrough, and thus, the patient is safe from being infected with bacteria.

In the drawings, the reference numeral 30 denotes a high frequency generator connected through a first wire 31 to the conductive body 15 and through a second wire 32 to a pad 35 attached to an external surface of a body of the patient, and the reference numeral 40 denotes a temperature measuring device to measure a temperature of the conductive body 15.

A detailed description will be given of the application of the stent according to the present invention to the patient referring to FIG. 6.

When a contracted portion of the internal cavity 100 caused by cancer tissues and malignant tumors is found, the stent according to the present invention is inserted into the internal cavity 100 of the patient using an insertion tool through a traditional procedure to expand the contracted target portion 110 of the internal cavity due to the elasticity of the stent.

In this respect, the stent according to the present invention has a double structure including the hollow cylindrical stent body 5 covered with the insulating substance 10 at an inner surface thereof and the cylindrical conductive body 15, surrounding the waist part 20 of the stent body 5, without being covered with the insulating substance 10.

Instead of the insulating substance 10, the conductive body 15 of the stent of the present invention directly comes into contact with the internal cavity 100 of the patient to expand the contracted target portion of the internal cavity 100, thereby preventing the stent from moving within the slippery internal cavity 100.

Furthermore, the high frequency generator 30 is connected through the first wire 31 to the conductive body 15 of the stent according to the present invention, and through the second wire 32 to the pad 35 attached to the external surface of the body of the patient.

In such a state, when the high frequency generator 30 is turned on, heat is emitted from the conductive body 15, due to a high frequency current, inserted into the contracted target portion of the internal cavity with the lesion to cauterize the lesion 110, such as cancer tissues or malignant tumors, around the conductive body 15 to necrotize the lesion 110.

In detail, the high frequency current is not applied to a portion of the internal cavity 100 coming into contact with the hollow cylindrical stent body 5 covered with the insulating substance 10, but to only the lesion 110 of the internal cavity 100 coming into contact with the conductive body 15 to cauterize the lesion 110 to necrotize only the lesion 110.

As well, the temperature of the conductive body 15 is measured using the temperature measuring device 40, and an intensity of the high frequency current applied to the internal cavity 100 is properly controlled according to the temperature of the conductive body 15 to regulate the degree of necrosis of the lesion 110.

After the completion of the necrosis of the lesion 110, the conductive body 15 is drawn out of the internal cavity 100 by pulling the first wire 31 connected to the conductive body 15, and the stent body 5 of the present invention is stayed within the internal cavity 100 while expanding the contracted portion of the internal cavity 100.

Meanwhile, the internal cavity 100 may be contracted again due to regeneration of the necrotized lesion 110. However, because the stent of the present invention has the double structure including the hollow cylindrical stent body 5 covered with the insulating substance 10 and the conductive body 15 surrounding the waist part 20 of the hollow cylindrical stent body 5, the insulating substance 10 of the stent functions to obstruct the lesion 110 from radially protruding through the diamond-shaped meshes 3 of the stent body 5 inward to prevent the internal cavity 100 from being re-contracted.

In other words, the stent having the double structure according to the present invention serves to completely prevent the internal cavity 100 with the regenerated lesion from being re-contracted.

As described above, both ends of the stent body 5 each have a larger diameter than the central part of the stent body 5, and the conductive body 15 surrounds the waist part 20 corresponding to the central part of the stent body 5. In this regard, the resulting structure of stent body 5 and the conductive body 15 combined with each other is of a cylindrical shape having a constant diameter therethroughout. Accordingly, the resulting stent structure is easily inserted into the internal cavity 100. Particularly, the conductive body 15 partially connected to the hollow cylindrical stent body 5 is easily contracted, thereby ease of the insertion of the stent into the internal cavity 100 is ensured.

The stent of the present invention may be fabricated by knitting the superelastic shape-memory alloy wires 2 according to a modified process that falls within meets and bounds of claims of the present invention, or equivalence of such meets and bounds are therefore intended to be embraced by the claims.

Because the first end 15a of the conductive body 15 is attached to the waist part 20 of the hollow cylindrical stent body 5 while the second end 15b of the conductive body 15 is not connected to the stent body 5, a heat concentration phenomenon may occur at the second end 15b of the conductive body 15, as shown in FIG. 3.

Figure 5:
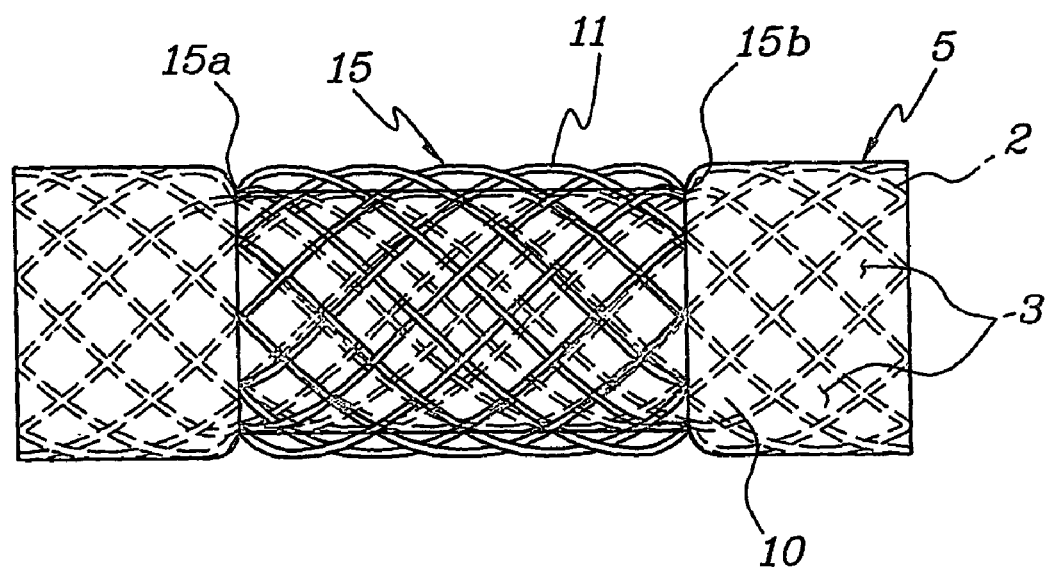
FIG. 5 illustrates a stent according to the second embodiment of the present invention.

In order to overcome such a problem, the stent according to the second embodiment of the present invention is structured such that the second end 15b of the conductive body 15 is attached to the waist part 20 of the stent body 5 as the first end 15a of the conductive body 15 is attached to the waist part 20 of the stent body 5 as shown in FIG. 5.

Figure 6:
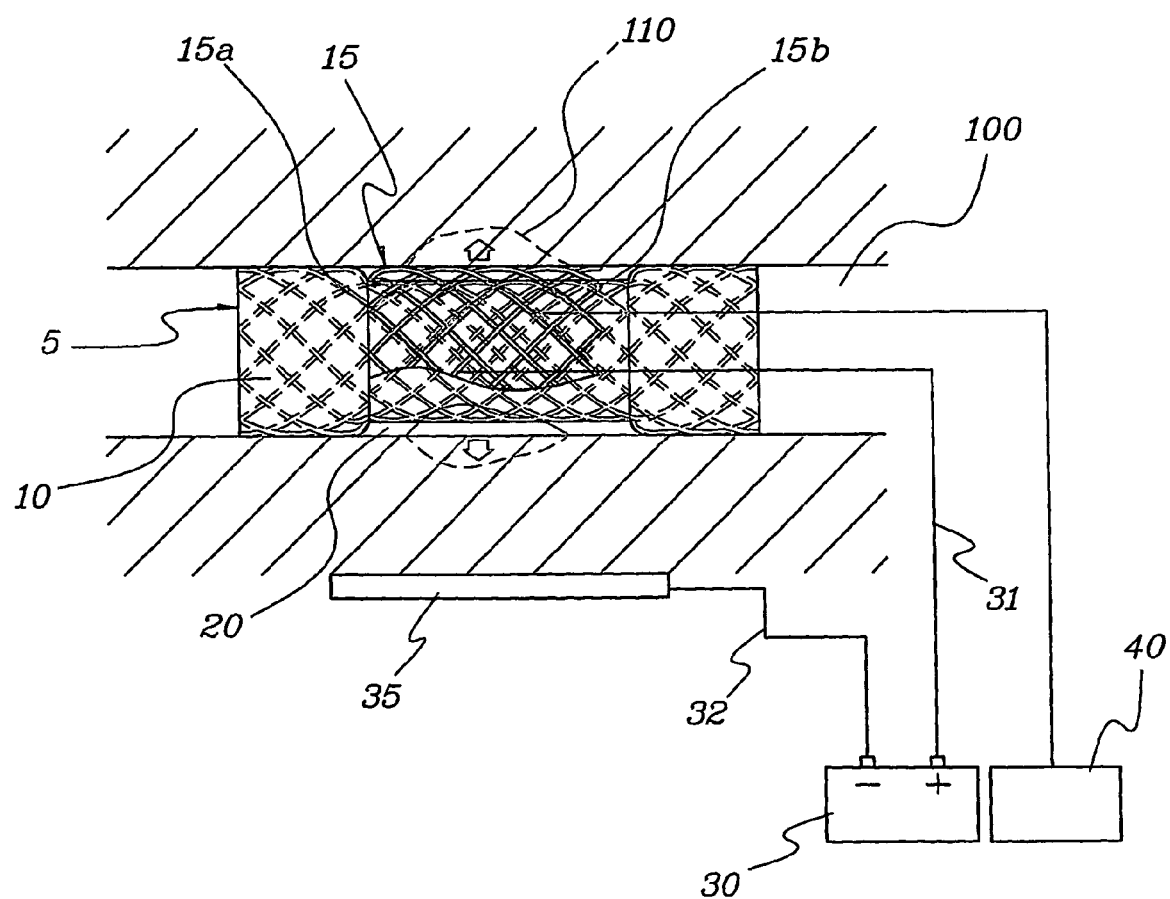
FIG. 6 is a view, showing the stent according to the present invention set within an internal cavity of a patient.

In such a case, the use of the stent equipped with the conductive body 15 with both its first and second ends 15a, 15b being attached to the waist part 20 of the stent body 5 is the same as the case of the stent equipped with the conducive body 15 having a structure in which only its first end 15a is attached to the waist part 20 of the stent body 5 as shown in FIG. 6.

INDUSTRIAL APPLICABILITY

As described above, the present invention provides a stent for high frequency thermotherapy, which has a double structure including a hollow cylindrical stent body covered with an insulating substance and a conductive body on which the insulating substance is not covered. Therefore, the stent effectively maintains its position within a contracted target portion of an internal cavity having a lesion when it is used to expand the contracted target portion of the internal cavity, and high-frequency heats the lesion of the internal cavity to cauterize the lesion to necrotize the lesion. Additionally, the stent obstructs the lesion from radially protruding inward to prevent the re-contraction of the internal cavity resulting from the regeneration of the lesion. Thereby, very high reliability of use of the stent is ensured.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A stent for insertion into a target portion of an internal cavity for high frequency thermotherapy, comprising:
   a hollow cylindrical stent body fabricated by knitting first superelastic shape-memory alloy wires in such a manner that the first superelastic shape-memory alloy wires cross each other at different positions to form the hollow cylindrical stent body having a predetermined length and a net structure with a plurality of meshes, wherein the hollow cylindrical stent body has an insulating substance covering inner and outer surfaces of the hollow cylindrical stent body, and an expanded diameter of the hollow cylindrical stent body is greater at a first end and a second end than at a waist part corresponding to a central part of the hollow cylindrical stent body; and
   a hollow cylindrical conductive body surrounding only the waist part or a portion thereof such that a first end of the hollow cylindrical conductive body is attached to the waist part of the hollow cylindrical stent body, the hollow cylindrical conductive body being fabricated by knitting second superelastic shape-memory alloy wires in such a manner that the second superelastic shape-memory alloy wires cross each other at different positions, and an expanded diameter of the hollow cylindrical conductive body is such that the hollow cylindrical conductive body comes into contact with the internal cavity to expand the target portion of the internal cavity,
   wherein an external expanded diameter of the stent is constant therethroughout.

2. A stent for insertion into a target portion of an internal cavity for high frequency thermotherapy, comprising:
   a hollow cylindrical stent body fabricated by knitting first superelastic shape-memory alloy wires in such a manner that the first superelastic shape-memory alloy wires cross each other at different positions to form the hollow cylindrical stent body having a predetermined length and a net structure with a plurality of meshes, wherein the hollow cylindrical stent body has an insulating substance covering inner and outer surfaces of the hollow cylindrical stent body, and an expanded diameter of the hollow cylindrical stent body is greater at a first end and a second end than at a waist part corresponding to a central part of the hollow cylindrical stent body; and
   a hollow cylindrical conductive body surrounding only the waist pan or a portion thereof such that a first end of the hollow cylindrical conductive body is attached to the waist part of the hollow cylindrical stent body, the hollow cylindrical conductive body being fabricated by knitting second superelastic shape-memory alloy wires in such a manner that the second superelastic shape-memory alloy wires cross each other at different positions, and an expanded diameter of the hollow cylindrical conductive body is such that the hollow cylindrical conductive body comes into contact with the internal cavity to expand the target portion of the internal cavity,
   wherein an expanded diameter of the first end and the second end of the stent body and the expanded diameter of the conductive body are equal.

3. The stent as set forth in claim 2, wherein an external expanded diameter of the stent is constant therethroughout as a result of the combination of the stent body and the conductive body structures.

4. A stent for insertion into a target portion of an internal cavity for high frequency thermotherapy, comprising:
   a hollow cylindrical stent body fabricated by knitting first superelastic shape-memory alloy wires in such a manner that the first superelastic shape-memory alloy wires cross each other at different positions to form the hollow cylindrical stent body having a predetermined length and a net structure with a plurality of meshes, wherein the hollow cylindrical stent body has an insulating substance covering inner and outer surfaces of the hollow cylindrical stent body, and an expanded diameter of the hollow cylindrical stent body is greater at a first end and a second end than at a waist part corresponding to a central part of the hollow cylindrical stent body; and
   a hollow cylindrical conductive body surrounding only the waist part or a portion thereof such that a first end of the hollow cylindrical conductive body is attached to the waist part of the hollow cylindrical stent body at a second end of the conductive body as well as the first end of the conductive body, the hollow cylindrical conductive body being fabricated by knitting second superelastic shape-memory alloy wires in such a manner that the second superelastic shape-memory alloy wires cross each other at different positions, and an expanded diameter of the hollow cylindrical conductive body is such that the hollow cylindrical conductive body comes into contact with the internal cavity to expand the target portion of the internal cavity,
   wherein the expanded diameter of the first end and the second end of the stent body and the expanded diameter of the conductive body we equal.

* * * * *